United States Patent
Taylor et al.

(10) Patent No.: US 6,900,331 B2
(45) Date of Patent: May 31, 2005

(54) DERIVATIVES OF EPOTHILONE B AND D AND SYNTHESIS THEREOF

(75) Inventors: Richard E. Taylor, South Bend, IN (US); Yue Chen, Mishawaka, IN (US)

(73) Assignee: University of Notre Dame, Notre Dame, IN (US)

( * ) Notice: Subject to any disclaimer, the term of this patent is extended or adjusted under 35 U.S.C. 154(b) by 0 days.

(21) Appl. No.: 10/375,100

(22) Filed: Feb. 28, 2003

(65) Prior Publication Data

US 2003/0176473 A1 Sep. 18, 2003

Related U.S. Application Data

(60) Provisional application No. 60/360,853, filed on Mar. 1, 2002.

(51) Int. Cl.$^7$ ............................................. C07D 277/20
(52) U.S. Cl. ...................................... 548/204; 548/203
(58) Field of Search .................................. 548/203, 204

(56) References Cited

U.S. PATENT DOCUMENTS

| | | | | |
|---|---|---|---|---|
| 6,262,094 B1 | * | 7/2001 | Hoefle et al. | 514/365 |
| 6,288,237 B1 | * | 9/2001 | Hoefle et al. | 548/203 |
| 6,380,227 B1 | * | 4/2002 | Mutz | 514/365 |
| 6,489,314 B1 | * | 12/2002 | Ashley et al. | 514/183 |
| 6,589,968 B2 | * | 7/2003 | Arslanian et al. | 514/365 |
| 6,613,912 B2 | * | 9/2003 | Hoefle et al. | 548/204 |
| 6,624,310 B1 | * | 9/2003 | Hoefle et al. | 548/204 |

* cited by examiner

*Primary Examiner*—Golam M M Shameem
(74) *Attorney, Agent, or Firm*—Jagtiani +Guttag

(57) ABSTRACT

The present invention provides the following new compounds: (R)-C14-methyl-epothilone B, (S)-C14-methyl-epothilone B, (S)-C14-methyl-epothilone D, and (R)-C14-methyl-epothilone D and methods for synthesizing these compounds.

12 Claims, 5 Drawing Sheets

Scheme 1

Scheme 2

Scheme 3

Scheme 4

13 (*R*)-14-methyl-epothilone D

14 (*S*)-14-methyl analogue

DERIVATIVES OF EPOTHILONE B AND D AND SYNTHESIS THEREOF

GOVERNMENT INTEREST STATEMENT

This invention is made with government support under Grant ID No. CA84599 awarded by the National Cancer Institute/NIH. The government may have certain rights in this invention.

BACKGROUND OF THE INVENTION

1. Field of the Invention

The present invention relates to derivatives of epothilone B and D.

2. Description of the Prior Art

Cancer still represents a major unmet medical need. Initial treatment of the disease is often surgery, radiation treatment or the combination, but recurrent (metastatic) disease is common. Chemotherapeutic treatments for most cancers are generally not curative, but only delay disease progression. Commonly, tumors and their metastases become refractory to chemotherapy, in an event known as development of multidrug resistance. In many cases, tumors are inherently resistant to some classes of chemotherapeutic agents.

Among cytotoxic agents for the treatment of tumors, TAXOL® (paclitaxel), a microtubule stabilizing agent, has become a very important compound with a remarkable economic success. However, TAXOL® has a number of disadvantages. Especially its extremely low solubility in water represents a severe problem. It has become necessary to administer TAXOL® in a formulation with Cremophor EL® (polyoxyethylated castor oil; BASF, Ludwigshafen, Germany) which has severe side effects, causing inter alia allergic reactions that in one case even were reported to have led to the death of a patient. More severely, certain tumor types are known to be refractory to treatment with TAXOL® even when the drug is administered as front-line therapy, or the tumors develop resistance to TAXOL® after multiple cycles of exposure.

Although the taxane class of antimicrotubule anti-cancer agents has been hailed as the perhaps most important addition to the chemotherapeutic armamentarium against cancer over the past several decades and despite the commercial success of TAXOL®, there remain limitations to TAXOL®'s efficacy. TAXOL® treatment is associated with a number of significant side effects and some major classes of solid tumors, namely colon and prostate, are poorly responsive to this compound. For example, the effectiveness of TAXOL® can be severely limited by acquired drug resistance mechanisms occurring via various mechanisms, such as overexpression of phosphoglycoproteins that function as drug efflux pumps.

Therefore, there exists an urgent need to find compounds and appropriate dosing regimens with these compounds to expand the armamentarium of cancer treatment, especially in the majority of cases where treatment with taxanes and other anticancer compounds is not associated with long term survival.

SUMMARY OF THE INVENTION

It is therefore an object of the present invention to provide new compounds that may be used effectively in cancer chemotherapy.

It is a further object of the present invention to provide compounds that may be used to treat TAXOL®-resistant tumors.

It is yet a further object of the present invention to provide new derivatives of epothilone B.

It is yet a further object of the present invention to provide new derivatives of epothilone D.

According to a first broad aspect of the present invention, there is provided compound comprising (R)-C14-methyl-epothilone B.

According to second broad aspect of the present invention, there is provided a compound comprising (S)-C14-methyl-epothilone B.

According to third broad aspect of the present invention, there is provided a compound comprising (S)-C14-methyl-epothilone D.

According to fourth broad aspect of the present invention, there is provided a compound comprising (R)-C14-methyl-epothilone D According to a fifth broad aspect of the present invention, there is provided a method for synthesizing (R)-C14-methyl-epothilone B comprising the steps of: providing (S)-C14-methyl-epothilone D; and (b) incorporating an epoxide group at the C12–C14 position of (S)-C14-methyl-epothilone D to form (R)-C14-methyl-epothilone B.

According to a sixth broad aspect of the invention, there is provided a method for synthesizing (S)-C14-methyl-epothilone D comprising the following steps:

(a) providing an ethyl ketone 10 having the following formula:

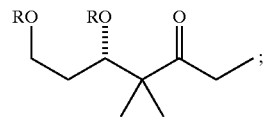

(b) exposing ethyl ketone 10 to LDA to produce the lithium enolate of ethyl ketone 10;
(c) mixing ethyl ketone 10 with an aldehyde 9 having the following formula:

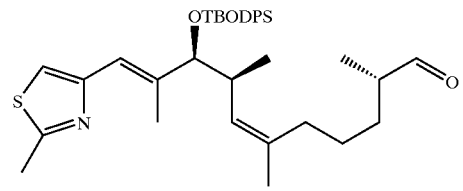

to thereby form a syn., anti-aldol adduct having a primary alcohol and a C7 hydroxyl;
(d) exposing said syn., anti-aldol adduct to TBSOTf to convert said C7 hydroxyl to a TBS ether;
(e) de-protecting said syn., anti-aldol adduct to form a primary alcohol;
(f) oxidizing said primary alcohol to form an oxidized adduct having a C1-carboxylic acid;
(g) removing a C15 TBODPS ether from said oxidized adduct to form a compound 11 having the following formula:

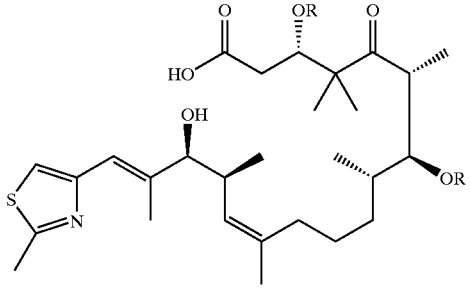

(h) macrolactonizing compound 11 to form a 16-membered lactone; and (i) treating said 16-membered lactone with TFA to form (S)-C14-methyl-epothilone D.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

It is advantageous to define several terms before describing the invention. It should be appreciated that the following definitions are used throughout this application.

Definitions and Abbreviations

For the purposes of the present invention, the term "scheme" refers to one or more sub-steps of a method for synthesizing an epothilone derivative of the present invention.

Figure 2:
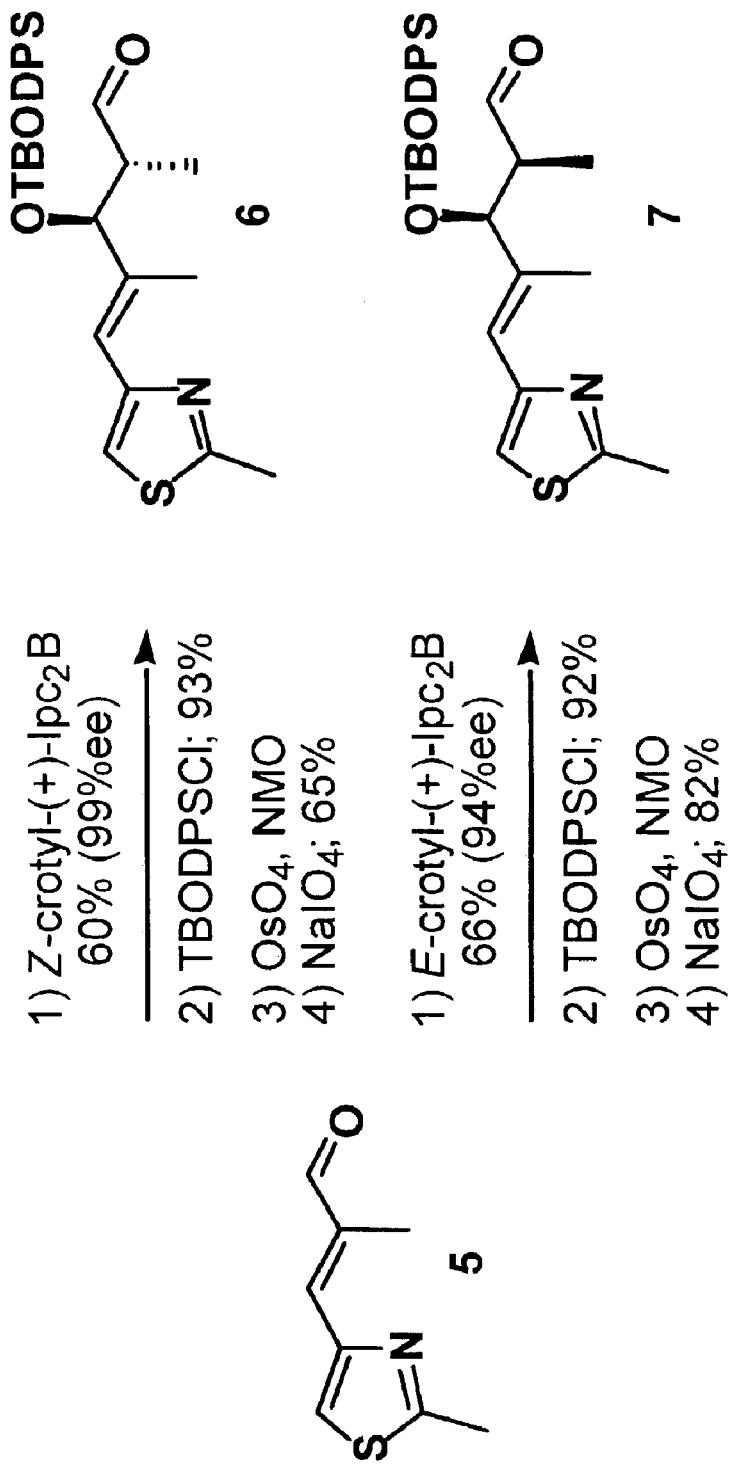
FIG. 2 illustrates a first scheme of a method of the present invention for forming first intermediates useful in synthesizing the epothilone B and D derivatives of the present invention.
Figure 3:
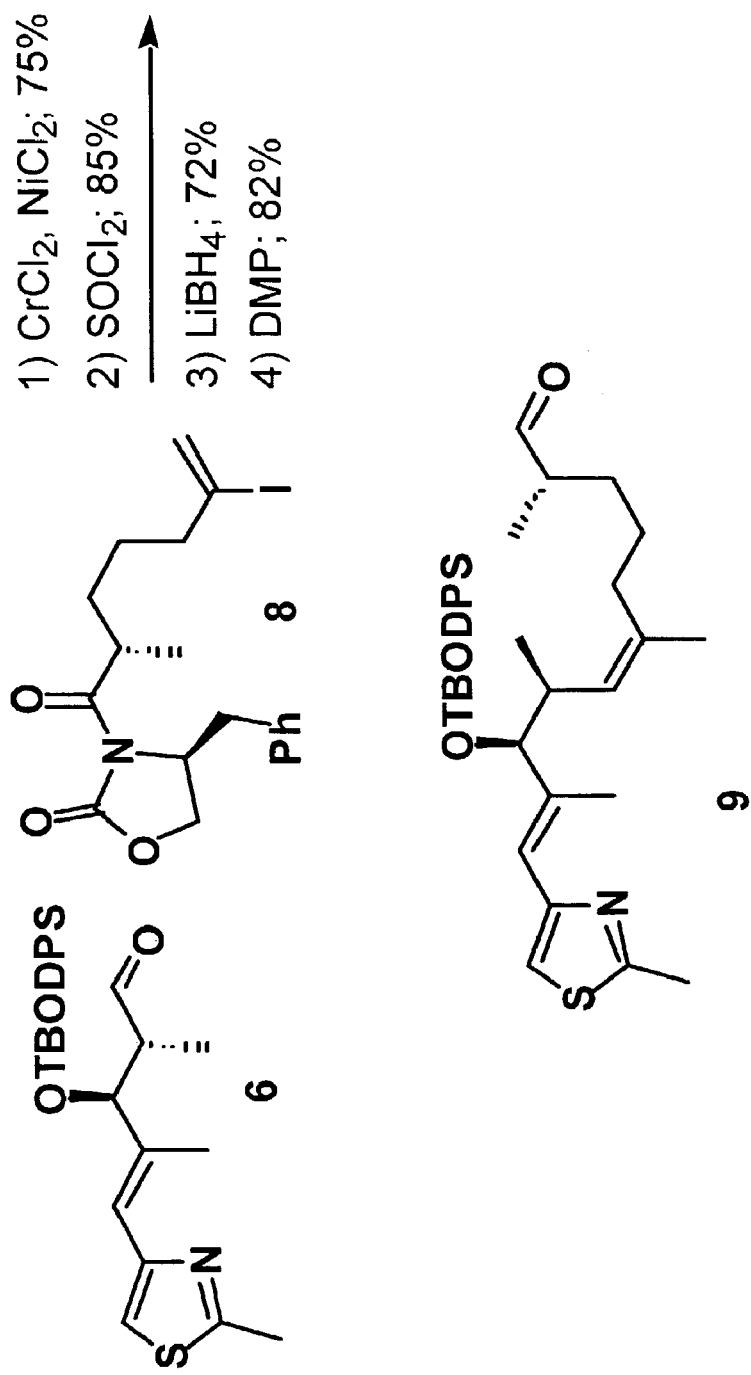
FIG. 3 illustrates a second scheme of a method of the present invention, using the first intermediates of FIG. 2, for forming second intermediates useful in synthesizing the epothilone B and D derivatives of the present invention.
Figure 4:
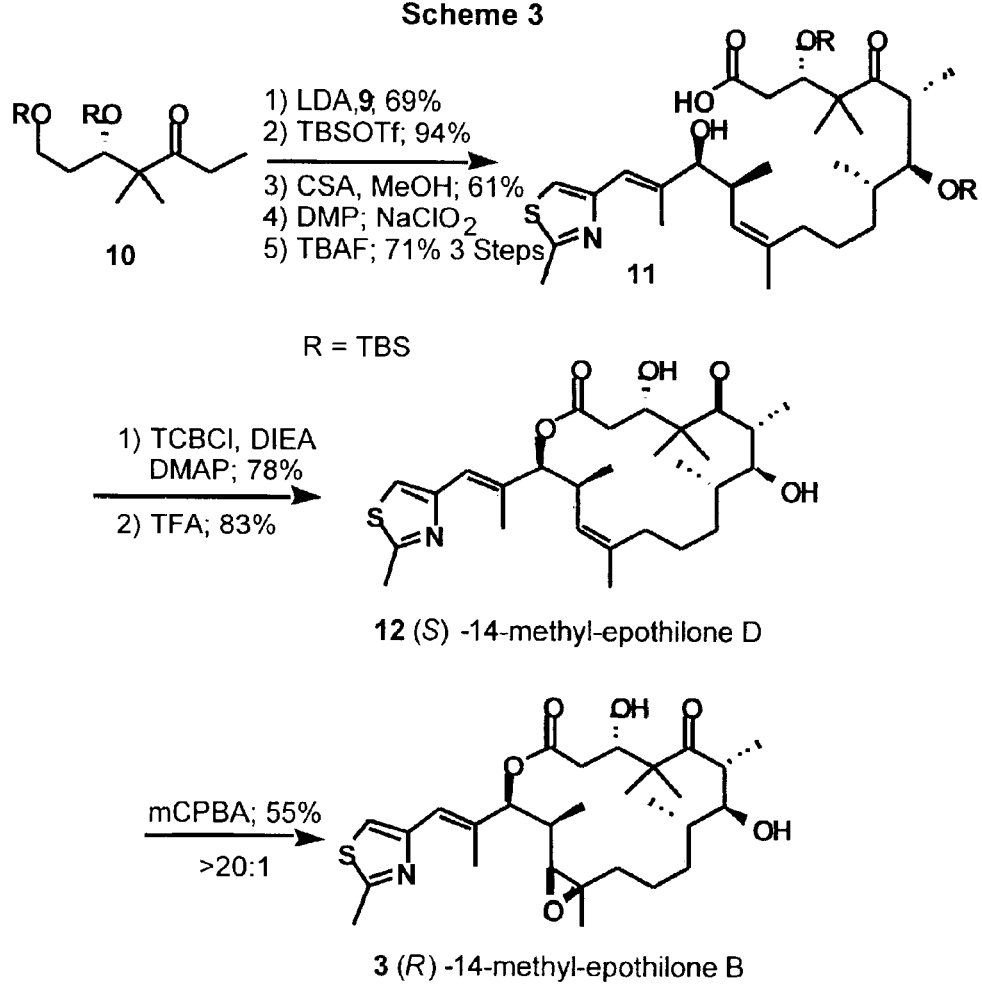
FIG. 4 illustrates a third scheme of a method of the present invention, using the second intermediates of FIG. 3 to form the epothilone B and D derivatives of the present invention.

The following abbreviations appear in Schemes 1, 2 and 3 of FIGS. 2, 3 and 4, respectively: Z-crotyl-(+)-Ipc₂B (Z-3-methylpropenyl-diisopinocampheyl borane), described in Brown, H. C. and Bhat, K. S. "Chiral Synthesis via Organoboranes. 7. Diastereoselective and Enantioselective Synthesis of Erythro- and Threo-β-methylhomoallyl Alcohols via Enantiomeric (Z)- and (E)-Crotylboranes" *J. Am. Chem. Soc.* 1986, 108, 5919–5923, the entire contents and disclosure of which is hereby incorporated by reference), NMO (4-methylmorpholine N-oxide) LDA (lithium diamine), TBODPSCl (t-butoxydiphenylsilyl chloride), TBSOTf (t-butyl-dimethylsilyltriflate) TBS (t-butyl-dimethylsilyl), CSA (camphorsulfonic acid), DMP (Dess-Martin periodinane, described in Dess D. B.; Martin J. C. "Readily Accessible 12-I-5 Oxidant for the Conversion of Primary and Secondary Alcohols to Aldehydes and Ketones" *J. Org. Chem.* 1983, 48, 4155–4156, the entire contents and disclosure of which is hereby incorporated by reference), TBAF (tetrabutylammonium fluoride, TCBCl (2,4,5-tichlorobenzoyl chloride), DIEA (N,N-diisopropylethylamine), DMAP (4-(dimethylamino) pyridine), TFA (trifluoroacetic acid), and mCPBA (m-Chloroperoxy benzoic acid).

Description

The success of the anticancer drug Taxol®, marketed by Bristol-Myers Squibb, appears to be related to its unique mode of action, tubulin polymerization and microtubule stabilization. However, Taxol®'s low water solubility and inactivity against multi-drug resistant tumors limits Taxol®'s usefulness. Compounds with biological activity related to Taxol®'s activity included the epothilones, but the known epothilones and epothilone derivatives are not satisfactory for all purposes. Several years ago, a study by Taylor et al. on the conformational properties of the epothilones which utilized a combination of computational methods and high field NMR experiments, see Taylor, R. E. and Zajicek, J. "The Conformational Properties of Epothilone" *J. Org. Chem.* 1999, 64, 7224. The Taylor et al. study concentrated on the critical C1–C8 polypropionate region and concluded that in solution the epothilones preferred to exist in at least two conformational families controlled by the syn-pentane interactions. In addition, the Taylor et al. study showed that the major contributor was indeed related to the conformation observed in the solid state, see also Hoefle, G.; Bedorf, N.; Steinmetz, H.; Schomburg, D.; Gerth, K.; and Reichenbach, H. "Epothilone A and B-Novel 16-membered Macrolides with Cytotoxic Activity: Isolation, Crystal Structure, and Conformation in Solution" *Angew. Chemie* 1996, 35, 1567–1569. The conversion of an allylic alcohol to an allylic chloride useful in synthesizing epothilone derivatives is described in Taylor, R. E.; and Chen, Y. "The Total Synthesis of Epothilones B and D" *Organic Lett.* 2001, 3, 2221, the entire contents and disclosure of which is hereby incorporated by reference.

The present invention provides epothilone derivatives and method of making epothilone derivatives based on the stabilization of conformational families through simple substitution. Several of the preferred epothilone derivatives of the present invention have significant biological activity and together provide new insights into the biological active conformation of the epothilone class of natural products.

The chemical formulas for epothilones A, B, C and D are shown below:

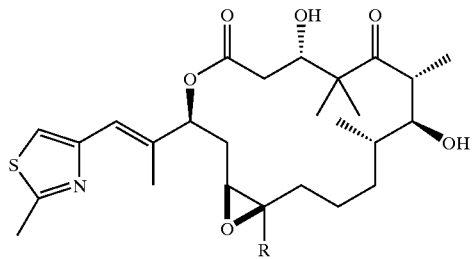

1a R = H  epothilone A
2a R = Me  epothilone B

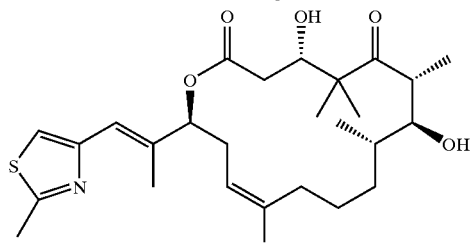

1b R = H  epothilone C
2b R = Me  epothilone D

Figure 1:
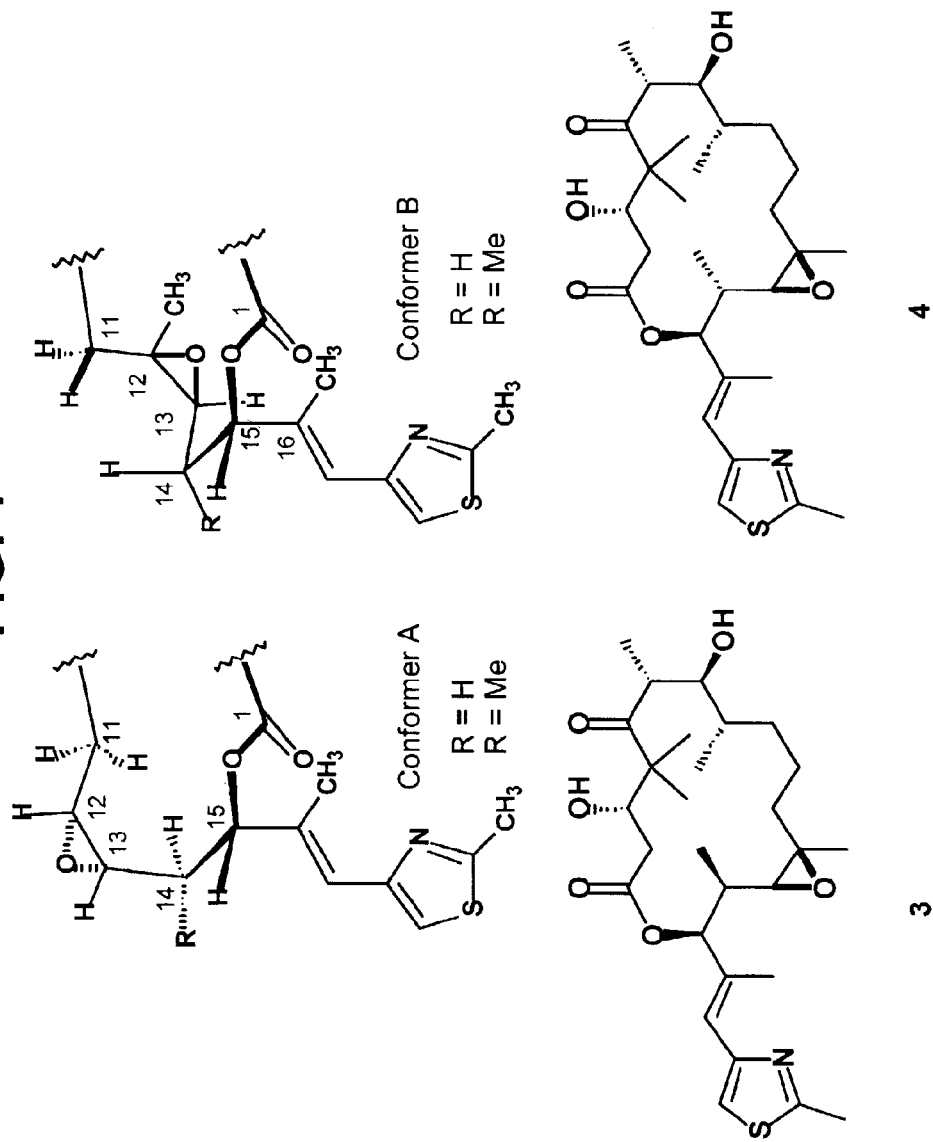
FIG. 1 illustrates two conformations of epothilone B and two derivatives of epothilone B.

With respect to the C10–C15 epoxide region of epothilone B and epothilone B derivatives, a high degree of flexibility leading to two conformational families shown as Conformer A and B, in which R=H for epothilone B and R=Me for the epothilone B derivative 3 ((R)-C14-methyl epothilone B) and epothilone B derivative 4 ((S)-C14-methyl epothilone B) of FIG. 1. The epothilone B derivatives 3 and 4 are intriguing because epothilone B derivatives 3 and 4 represent an acetate to propionate modification in the biogenetic pathway. Therefore, advances in genetic engineering of polyketide synthases, see Khosla, C. "Natural Product Biosynthesis: A New Interface between Enzymology and Medicine" J. Org. Chem. 2000, 65, 8127–8133, may provide alternative methods, in addition to the chemical synthesis methods described below, for producing epothilone B derivative 3 through manipulation of the epothilone gene cluster, see Julien, B.; Shah, S.; Ziermann, R.; Goldman, R.; Katz, L.; and Khosla, C. "Isolation and Characterization of the Epothilone Biosynthetic Gene Cluster from *Soranium cellulosum*" Gene 2000, 249, 153–160. b) Tang, L.; Shah, S.; Chung, L.; Carney, J.; Katz, L.; Khosla, C.; and Julien, B. *Science* 2000, 287, 640–642. c) Molnar, I.; Schupp, T.; Ono, M.; Zirkle, R.; Milnamow, M.; Nowak-Thompson, B.; Engel, N.; Toupet, C.; Stratmann, A.; Cyr, D. D.; Gorlach, J.; Mayo, J. M.; Hu, A.; Goff, S.; Schmid, J.; and Ligon, J. M. "The Biosynthetic Gene Cluster for the Microtubule-Stabilizing Agents Epothilones A and B from Sorangium cellulosum So ce90" *Chem. Biol.* 2000, 7, 97–109, or through semi-synthesis/biosynthetic techniques used on *Sorangium cellulosum*, the organism from which epothilones are generally produced.

In a preferred method of the present invention, (S)-C14-methyl-epothilone D is synthesized using thiazole aldehyde 5 of Scheme 1 of FIG. 2. A brown asymmetric crotylboration using Z-crotyl-(+)-Ipc$_2$B to form compound 5a having the following formula:

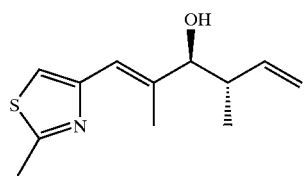
(5a)

Compound 5a is treated with TBODPSCl to protect the secondary hydroxyl of Compound 5a as t-butoxydiphenylsilyl ether and form compound 5b having the following formula:

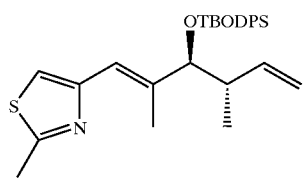
(5b)

An oxidative cleavage of the terminal alkene using OsO$_4$, NMO followed by NaIO$_4$ may be performed on compound 5b to form aldehyde 6 of Scheme 1.

Next, a vinyl aldehyde 8, shown in Scheme 2 of FIG. 3, is intermolecularly coupled with aldehyde 6 using Ni/Cr coupling to provide an intermediate allylic alcohol 8a having the following formula as a mixture of diastereomers (1:1).:

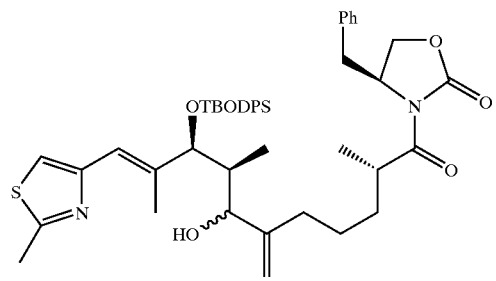
(8a)

Exposure of this mixture to thionyl chloride in ether-pentane provides a primary allylic chloride 8b having the following formula:

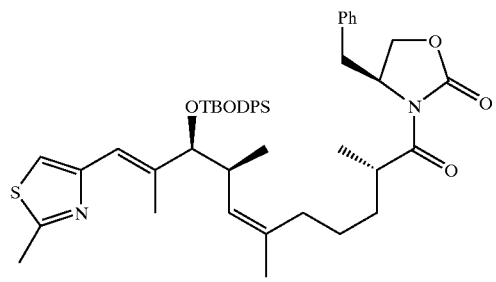
(8b)

Reacting the primary allylic chloride 8b with LiEt$_3$BH form a primary alcohol 8c having the following formula:

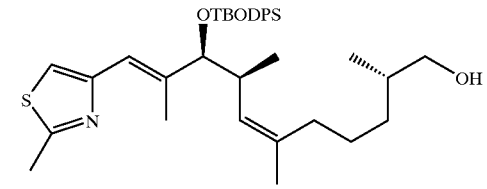
(8c)

Primary alcohol 8c is then oxidized with Dess-Martin periodane to provide aldehyde 9 of Scheme 2.

Next, ethyl ketone 10 shown in Scheme 3 of FIG. 4 is reacted with LDA and aldehyde 9 to form a syn, anti-aldol adduct 11a having the following formula:

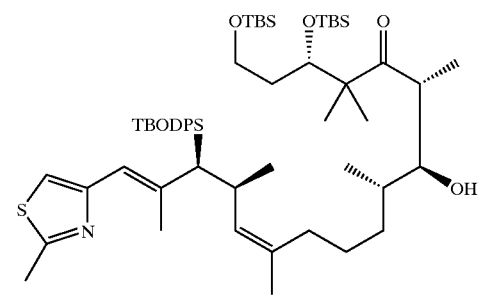
(11a)

The C7 hydroxyl of syn, anti-aldol adduct 11a is protected as a TBS ether by reacting syn, anti-aldol adduct 11a with TBSOTf to form an etherized adduct 11b having the following formula:

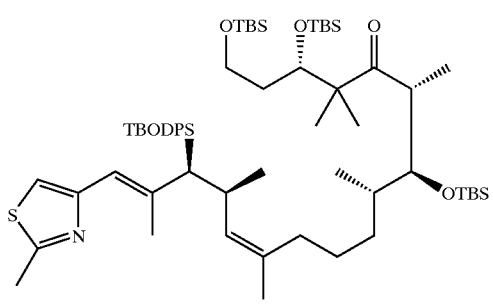

(11b)

Etherized adduct 11b is exposed to acidic methanol solution to liberate a primary alcohol 11c having the following formula:

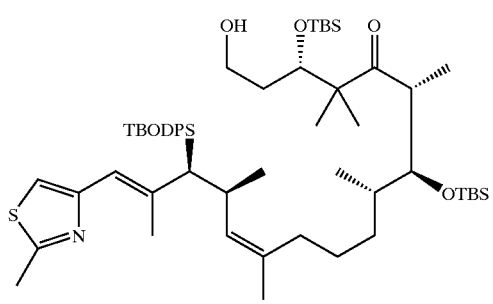

(11c)

Primary alcohol 11c is the treated with DMP to provide aldehyde 11d having the following formula:

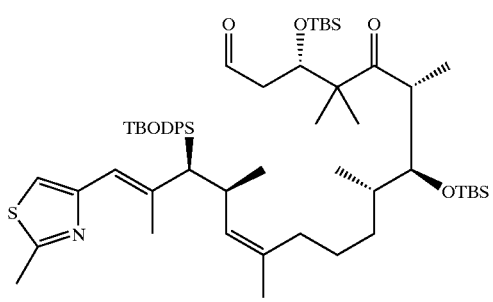

(11d)

Aldehyde 11d is then oxidized to a carboxylic acid, oxidized adduct 11e having the following formula:

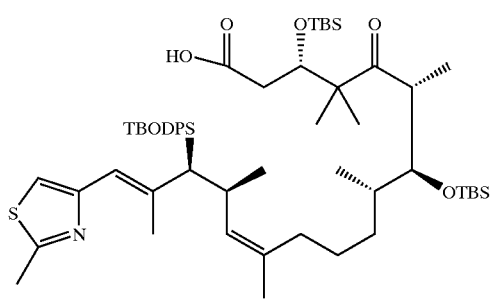

(11e)

Oxidized adduct 11e is then treated with TBAF to remove the C15 TBSDPS ether to form alcohol 11 of Scheme 3 of FIG. 4. A macrolactonization is then carried out on alcohol 11 using TCBCl, DIEA and DMAP to form a 16-membered lactone 12a having the following formula:

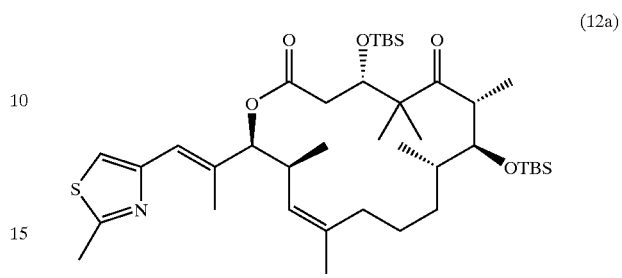

(12a)

A deprotection of the C3 and C7 silyl ethers of lactone 12a is then carried out using TFA to form (S)-C14-methyl epothilone D 12b having the following formula:

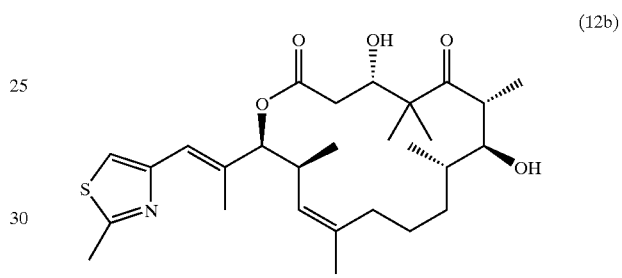

(12b)

In a preferred method of the present invention, (R)-C14-methyl-epothilone B is synthesized by exposing (S)-C14-methyl-epothilone D to mCPBA.

A method similar to the method described above for synthesizing (S)-C14-methyl-epothilone D from thiazole aldehyde 5 may be used to synthesize (R)-C14-methyl-epothilone D by carrying out the crotylboration of thiazole aldehyde 5 with E-crotyl-(+)-Ipc$_2$B instead of Z-crotyl-(+)-Ipc$_2$B to form aldehyde 7 instead of aldehyde 6. The remaining synthesis steps to form (R)-C14-methyl-epothilone D from aldehyde 7 are similar to the synthesis steps used to form (S)-C14-methyl-epothilone D from aldehyde 6.

In a preferred method of the present invention, (S)-C14-methyl-epothilone B may be synthesized by exposing (R)-C14-methyl-epothilone D to mCPBA.

EXAMPLES

Example 1

(R)-C14-methyl epothilone B (epothilone B derivative 3) was synthesized using a method shown in Schemes 1, 2 and 3 of FIGS. 2, 3 and 4, respectively.

Readily available thiazole aldehyde 5, a common intermediate in several synthetic routes to these epothilone, is the point divergence for the synthesis of epothilone B derivatives 3 and 4 as shown in Scheme 1. Brown asymmetric crotylboration[9] efficiently controlled the enantioselectivity as well as the diastereoselectivity of the C14, 15 stereogenic centers. Protection of the secondary hydroxyl as a t-butoxydiphenylsilyl ether followed by oxidative cleavage of the terminal alkene provided aldehydes 6 and 7.

The conversion of aldehydes 6 and 7 to epothilone B derivatives 3 and 4, respectively, proceeded though identical synthetic sequences. Only the synthesis of epothilone B derivative 3 from aldehyde 6 is described below and shown in Schemes 2 and 3, of FIGS. 3 and 4, respectively. However, (S)-14-methyl epothilone B (epothilone B derivative 4) may be synthesized in a similar manner by substituting aldehyde 7 for aldehyde 6 in the first step of Scheme 2 of FIG. 3.

As shown in Scheme 2 of FIG. 3, intermolecular Ni/Cr coupling of vinyl iodide 8 with aldehyde 6 (2 equiv.) provided the intermediate allylic alcohol in 75% yield as a mixture of diastereomers (1:1). Exposure of this mixture to thionyl chloride in ether-pentane provided the desired primary chloride in 85% yield. While the olefin geometry was completely selective a small amount of the secondary allylic chloride could be observed in the crude proton NMR spectrum. LiEt$_3$BH not only reductively cleaved the chiral auxiliary but also efficiently reduced the allylic chloride in 72% yield providing primary alcohol 8c. Oxidation with Dess-Martin periodinane then provided aldehyde 9.

As highlighted in Scheme 3 of FIG. 4, the completion of the total synthesis began with an aldol reaction. The lithium enolate of ethyl ketone 10 was generated by exposure to LDA at −78° C. Addition of aldehyde 9 provided the desired syn, anti-aldol adduct as the major product in 69% yield and 3.5:1 selectivity. After protection of the C7 hydroxyl as a TBS ether the primary alcohol was liberated by exposure to acidic methanol solution. The C1-carboxylic acid 11 was generated by two-step oxidation and subsequent selective removal of the C15 TBODPS (t-butoxydiphenylsilyl) ether was then accomplished with TBAF in a combined 71% yield. Macrolactonization proceeded efficiently using the Yamaguchi method[12] to provide the 16-membered lactone in 78% yield. Deprotection of the C3 and C7 silyl ethers was carried out using TFA providing the (S)-C14-methyl epothilone D 12. Finally, a highly selective incorporation of the C12–C13 epoxide was carried out by exposure to mCPBA yielding (R)-C14-methyl epothilone B in 55% yield.

Figure 5:
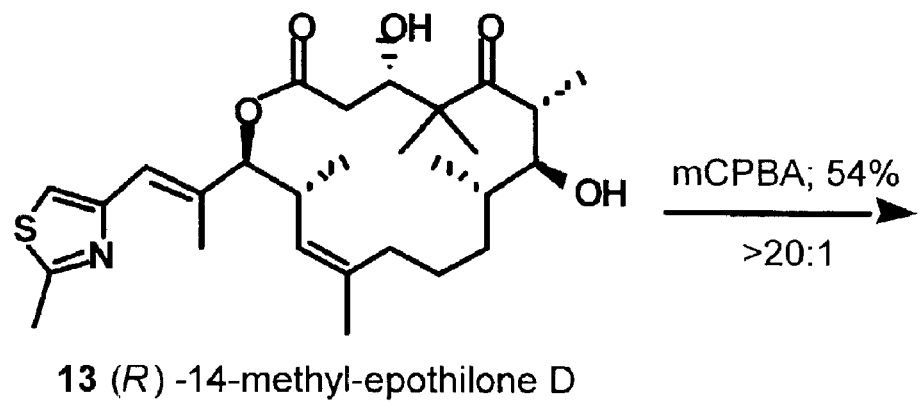
FIG. 5 illustrates a method of the present invention for forming an epothilone B derivative of the present invention from an epothilone D derivative of the present invention.
Figure 5:
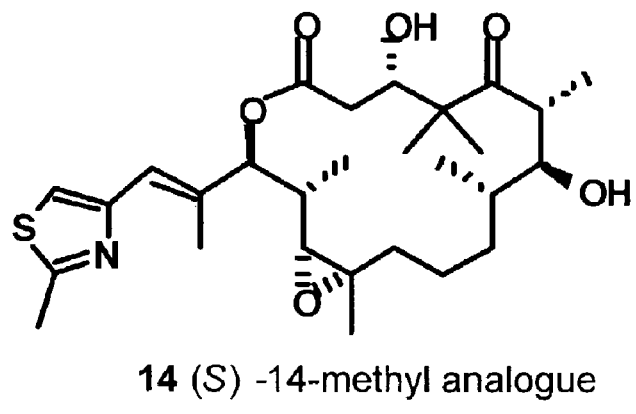

Synthesis of (R)-C14-methyl epothilone D, epothilone D derivative 13 was accomplished via a similar synthetic sequence to that described for the synthesis of (R)-C14-methyl epothilone D. Epoxidation of this intermediate proceeded in a highly selective fashion as shown in Scheme 4 of FIG. 5. The conformational constraints imposed by the C14-methyl substituent makes it highly likely that the stereochemistry of the epoxide is epimeric to epothilone B and epothilone derivatives 3 and 4. The resulting epothilone derivative appears to have the structure shown at 14.

Single crystals of epothilone D derivative 12 and epothilone B derivative 3 were obtained by slow-evaporation techniques and x-ray diffraction studies unambiguously determined their structure, FIG. 2. In addition, the conformation of each in the solid-state was quite similar to that reported for epothilone B and thus confomer A. Proton NMR coupling constants ($J_{14-15}$=9.9, 10.5 Hz respectively) also supported this preference in solution. In contrast, proton NMR coupling constants of epothilone derivatives 13 and 14 had the expected values for conformer B ($J_{14-15}$=2.9, 1.2 Hz respectively).

Preliminary biological investigations of these compounds revealed significant tubulin polymerization activity for compounds 12 and 3. In contrast, the C14-diastereomeric compounds, epothilone derivatives 13 and 14, showed relatively weak activity. Similar profiles were observed in tumor cell growth assays. In fact, (R)-C14-methyl-epothilone B 3 was found to be >2× as active as epothilone B itself.

The conformation-activity relationships presented herein strongly support the importance of conformer A for the tubulin binding Moreover, this approach represents on new perspective on rational design of new chemotherapeutic agents.

The synthesis methods described above for epothilone derivatives 3 and 4 was highlighted by the efficient generation of a C12–C13 trisubstituted olefin which exploits a sequential Nozaki-Hiyama-Kishi coupling and a stereoselective thionyl chloride rearrangement. Using the above-described synthesis method, quantities of epothilone derivatives 3 and 4 may be produced.

Example 2

Materials and Methods

Cell lines and culture conditions: Human breast carcinoma cell line MCF-7, multi-drug resistant breast carcinoma cell line NCI/ADR, non-small cell lung carcinoma cell line NCI-H460 and glioma cell line SF-268 were obtained from the National Cancer Institute. All cell lines were maintained in RPMI-1640 medium (Gibco/BRL, Rockville, Md.) supplemented with 2 mM L-glutamine, 25 mM HEPES and 10% FBS (Hyclone, Logan, Utah). Cells were maintained in a humidified incubator at 37° C. in 5% $CO_2$.

Cytoloxicity assays: Tumor cells were seeded in 100 μl at 5000 (MCF-7), 7500 (NCI/ADR), 5000 (NCI-H460) and 7500 (SF-268) cells per well in 96-well plates. Cells were allowed to adhere for 24 hours. Each compound ranging from 0.001 to 1000 nM in 100 μl was added to cells in triplicate wells. After 3 days, cells were fixed at 4° C. for 1 hour with 10% trichloroacetic acid and then stained with 0.2% sulforhodamine B (SRB)/1% acetic acid for 20 minutes at room temperature. The unbounded dye was rinsed away with 1% acetic acid, and the bounded SRB was then extracted with 200 μl of 10 mM Tris base. The absorbance was measured at 515 nm using a 96-well microtiter plate reader (Spectra Max 250, Molecular Devices). The $IC_{50}$ values were calculated using a KaleidaGraph program. The experiments were performed twice.

| Results $IC_{50}$ (nM) Values | | | | |
|---|---|---|---|---|
| Compound | MCF-7 | NCI-ADR | H460 | SF |
| Epothilone D | 5 | 26 | 20 | 7 |
| 14s-methyl Epothilone D | 35 | 238 | 42 | 42 |
| 14r-methyl Epothilone B | 3 | 23 | 3 | 3 |
| 14r-methyl Epothilone D | >1000 | >1000 | >1000 | >1000 |
| 14s-methyl Epothilone B | >1000 | >1000 | >1000 | >1000 |

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A compound having the formula (R)-C14-methyl-epothilone B.

2. A compound having the formula (S)-C14-methyl-epothilone B.

3. A compound having the formula (S)-C14-methyl-epothilone D.

4. A compound having the formula (R)-C14-methyl-epothilone D.

5. A method for synthesizing (R)-C14-methyl-epothilone B comprising the steps of:
   (a) providing (S)-C14-methyl-epothilone D; and
   (b) incorporating an epoxide group at the C12–C13 position of (S)-C14-methyl-epothilone D to form (R)-C14-methyl-epothilone B.

6. The method of claim 5, wherein step (b) is carried out by exposing (S)-C14-methyl-epothilone D to mCPBA.

7. The method of claim 5, wherein (S)-C14-methyl-epothilone D is provided by synthesizing (S)-C14-methyl-epothilone D by a method comprising the following steps:
   (c) providing an ethyl ketone 10 having the following formula:

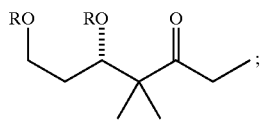

(d) exposing ethyl ketone 10 to LDA to produce the lithium enolate of ethyl ketone 10;
   (e) mixing ethyl ketone 10 with an aldehyde 9 having the following formula:

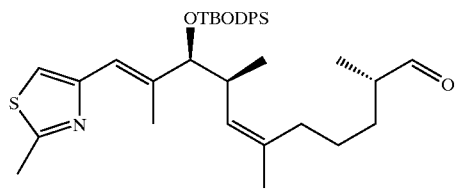

to thereby form a syn., anti-aldol adduct having a primary alcohol and a C7 hydroxyl;
   (f) exposing said syn., anti-aldol adduct to TBSOTf to convert said C7 hydroxyl to a TBS ether;
   (g) de-protecting said syn., anti-aldol adduct to form a primary alcohol;
   (h) oxidizing said primary alcohol to form an oxidized adduct having a C1-carboxylic acid;
   (i) removing a C15 TBODPS ether from said oxidized adduct to form a compound 11 having the following formula:

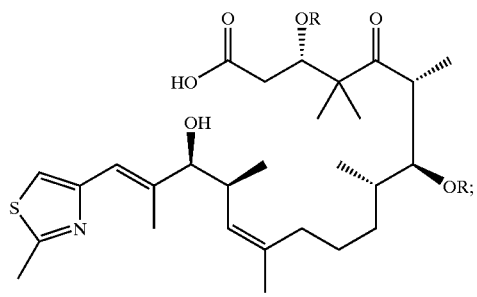

(j) macrolactonizing compound 11 to form a 16-membered lactone; and
   (k) treating said 16-membered lactone with TFA to form (S)-C14-methyl-epothilone D.

8. The method of claim 7, wherein aldehyde 9 is synthesized by a method comprising the following steps:
   (l) providing aldehyde 6 having the following formula:

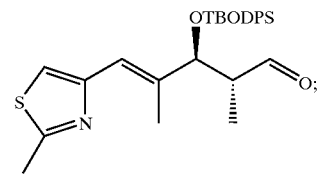

(m) intermolecularly coupling aldehyde 6 with a vinyl iodide 8 having the following formula:

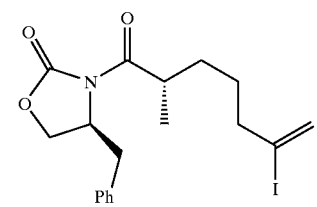

using Ni/Cr coupling to thereby form an intermediate allylic alcohol;
   (n) reacting said allylic alcohol thionyl chloride to produce a primary allylic chloride;
   (o) reacting said primary allylic chloride with LiEt$_3$BH to form a primary allylic alcohol; and
   (p) oxidizing said primary allylic alcohol to form aldehyde 9.

9. The method of claim 8, wherein aldehyde 6 is provided by synthesizing aldehyde 6 using a method comprising the following steps:
   (q) providing thiazole aldehyde 5 having the following formula:

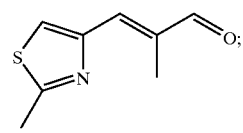

(r) reacting thiazole aldehyde 5 with Z-crotyl(+)-Ipc$_2$B to form a homoallylic alcohol compound;
   (s) reacting said homoallylic alcohol with TBODPSCl to form an etherized compound; and
   (t) oxidatively cleaving a terminal alkene of said etherized compound to form aldehyde 6.

10. A method for synthesizing (S)-C14-methyl-epothilone D comprising the following steps:
    (a) providing an ethyl ketone 10 having the following formula:

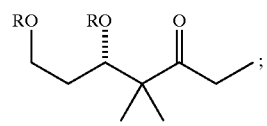

(b) exposing ethyl ketone 10 to LDA to produce the lithium enolate of ethyl ketone 10;

(c) mixing ethyl ketone 10 with an aldehyde 9 having the following formula:

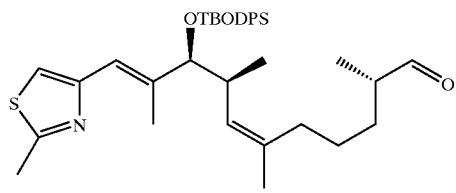

to thereby form a syn., anti-aldol adduct having a primary alcohol and a C7 hydroxyl;

(d) exposing said syn., anti-aldol adduct to TBSOTf to convert said C7 hydroxyl to a TBS ether;

(e) de-protecting said syn., anti-aldol adduct to form a primary alcohol;

(f) oxidizing said primary alcohol to form an oxidized adduct having a C1-carboxylic acid;

(g) removing a C15 TBODPS ether from said oxidized adduct to form a compound 11 having the following formula:

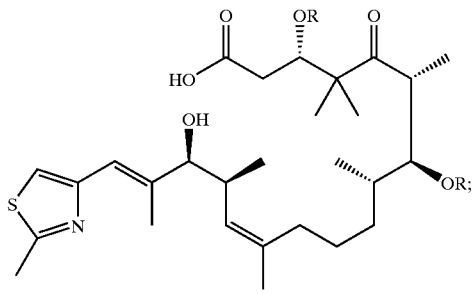

(h) macrolactonizing compound 11 to form a 16-membered lactone; and (i) treating said 16-membered lactone with TFA to form (S)-C14-methyl-epothilone D.

11. The method of claim 10, wherein aldehyde 9 is synthesized by a method comprising the following steps:

(j) providing aldehyde 6 having the following formula:

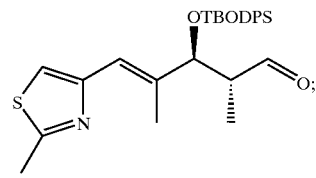

(k) intermolecularly coupling aldehyde 6 with a vinyl iodide 8 having the following formula:

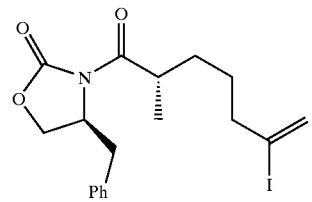

using Ni/Cr coupling to thereby form an intermediate allylic alcohol;

(l) reacting said allylic alcohol thionyl chloride to produce a primary allylic chloride;

(m) reacting said primary allylic chloride with LiEt$_3$BH to form a primary allylic alcohol; and (n) oxidizing said primary allylic alcohol to form aldehyde 9.

12. The method of claim 10, wherein aldehyde 6 is provided by synthesizing aldehyde 6 using a method comprising the following steps:

(o) providing thiazole aldehyde 5 having the following formula:

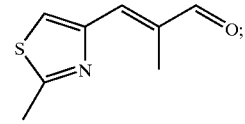

(q) reacting thiazole aldehyde 5 with Z-crotyl(+)-Ipc$_2$B to form a chloroborated compound;

(r) reacting said chloroborated aldehyde with TBODPSCl to form an etherized compound; and (s) oxidatively cleaving a terminal alkene of said etherized compound to form aldehyde 6.

* * * * *